(12) United States Patent
Perrin et al.

(10) Patent No.: US 6,638,717 B2
(45) Date of Patent: *Oct. 28, 2003

(54) MICROARRAY-BASED SUBTRACTIVE HYBRIDZATION

(75) Inventors: Steven Perrin, Newton, MA (US); Kathy Call, Malden, MA (US); Timothy Connolly, Belmont, MA (US)

(73) Assignee: Aventis Pharmaceuticals, Inc., Bridgewater, NJ (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/314,698

(22) Filed: May 19, 1999

(65) Prior Publication Data

US 2002/0051970 A1 May 2, 2002

(51) Int. Cl.⁷ .................................................. C12Q 1/68
(52) U.S. Cl. ......................................................... 435/6
(58) Field of Search .................... 435/6, 91.2; 536/24.3

(56) References Cited

U.S. PATENT DOCUMENTS

| | | | |
|---|---|---|---|
| 5,445,934 A | 8/1995 | Fodor | 435/6 |
| 5,589,339 A | 12/1996 | Hampson | 435/6 |
| 5,690,894 A | * 11/1997 | Pinkel et al. | 422/68.1 |
| 5,728,529 A | 3/1998 | Metzker | 435/6 |
| 5,800,992 A | 9/1998 | Fodor | 435/6 |
| 5,821,058 A | 10/1998 | Smith | 435/6 |
| 5,827,658 A | 10/1998 | Liang | |
| 5,830,662 A | 11/1998 | Soares | 435/6 |
| 5,846,721 A | 12/1998 | Soares | 435/6 |
| 5,851,772 A | 12/1998 | Mirzabekov | 435/6 |
| 5,882,874 A | 3/1999 | Fisher | 435/6 |
| 5,953,727 A | * 9/1999 | Maslyn et al. | 707/104 |

FOREIGN PATENT DOCUMENTS

| | | |
|---|---|---|
| WO | WO 97/41260 | 11/1997 |
| WO | WO 98/08973 | 3/1998 |
| WO | WO 98/43088 | 10/1998 |
| WO | WO 99/15702 | 4/1999 |
| WO | WO 99/23256 | 5/1999 |

OTHER PUBLICATIONS

Schena et al. Science vol. 270. Oct. 1995. pp. 467–470.*
Gress et al. Mammalian Genome. 3: 609–619, 1992.*
Beltz, et al., Methods in Enzymology, 100:266–285 (1983).
Botwell, nature genetics supplement, 21:25–32 (1999).
Heller, et al., Proc. Natl. Acad. Sci. USA, 94:2150–55 (1997).
Nguyen, et al., Genomics, 29:207–216 (1995).
Schena, et al., Proc. Natl. Acad. Sci. USA, 93:10614–10619 (1996).
International Search Report dated Oct. 10, 2000.
Adams, et al., Science, 252, 1651–1656 (1991).
Boguski & Schuler, Nat. Genetics. 10, 369–371 (1995).
Botwell, D.L., Nat. Genetics, 21, 25–29 (1999).
Brown & Botstein, Nat. Genetics, 21, 33–37 (1999).
Dovichi, Electrophoresis, 18, 2393–2399 (1997).
Duggan, et al., Nat. Genetics, 21, 10–14 (1999).
Ermolaeva, et al., Nat. Genetics, 20, 19–23 (1998).
Galau et al, Arch. Biochem Biophys, 179, 584–599 (1977).
Hacia, J.G., Nat. Genetics, 21, 42–47 (1999).
Ko, Nucleic Acids Res., 18, 5705–5711 (1990).
Lipshutz, et al. Nat. Genetics, 21, 20–24 (1999).
Luckey et al., Nucleic Acids Res., 18, 4417–4421 (1990).
Prober, et al., Science, 238, 336–341 (1987).
Smith, et al., Nature, 321, 674–679 (1986).
Weissman, Mol. Biol.Med., 4, 133–143 (1987).

* cited by examiner

*Primary Examiner*—Jeffrey Fredman
*Assistant Examiner*—Juliet C. Switzer
(74) *Attorney, Agent, or Firm*—Mintz, Levin, Cohn, Ferris, Glovsky and Popeo, P.C.; Ivor R. Elrifi, Esq.; Ingrid A. Beattie, Esq.

(57) ABSTRACT

The present invention relates to a highly efficient, high-throughput method for the identification and elimination of redundancy in a population of nucleic acid molecules using microarrays. This method involves a reiterative subtraction protocol that creates a library that becomes more biased toward unknown genes with each successive round. The removal of repetitive and previously characterized nucleic acids from the library allows the identification of low-abundance mRNA from sources of interest and enhances the rate of novel gene discovery. The present invention is also useful for the removal of contaminating nucleic acids from cloning libraries.

5 Claims, 4 Drawing Sheets

MICROARRAY-BASED SUBTRACTIVE HYBRIDZATION

FIELD OF THE INVENTION

The present invention relates to methods for the identification and isolation of nucleic acid fragments. More specifically, the invention covers methods for the identification and isolation of non-redundant mRNAs and novel genomic sequences.

BACKGROUND OF THE INVENTION

The elucidation of the mechanisms that dictate the normal functioning of living cells requires a detailed understanding of the information encoded in all of the complete genome. Messenger RNA (mRNA) sequences are typically used to map and sequence the genes contained in the genomes of different organisms. The sequence information is used to evaluate the genetic makeup of a particular cell or organism of interest. However, mRNAs are produced at different levels within different cell types and during different points in development. The distribution of mRNA types, their developmental and cell-type specific regulated expression, and their translation into protein produce the unique character of a particular cell type.

There are currently several world-wide research efforts aimed at cloning, mapping, and sequencing the genomes of various organisms, including *Homo sapiens*. Information from these projects will assist in providing an understanding of how genomes result in the organisms they specify. Furthermore, an understanding of the molecular makeup of normal functioning cells is essential to the understanding of various cellular processes—including the diagnosis and treatment of diseases in which regulation and expression of one or more of the genes has changed.

Integral to this goal is the production of libraries of cloned nucleic acids. Two different types of DNA libraries are typically used in the art. The first type, genomic libraries, are constructed by placing randomly cleaved DNA fragments of an entire genome into a suitable cloning vector. Although some of the clones in a genomic library contain genes or portions of genes, most clones contain non-coding DNA.

The second type of DNA libraries are complementary DNA (cDNA) libraries. These libraries are constructed from DNA that is reverse transcribed from mRNA isolated from a source of interest; cDNA libraries primarily contain DNA that codes for genes. However, different species of mRNA are not equally represented in a given cell. These mRNA molecules are distributed into three frequency classes: (1) superprevalent (consisting of approximately 10–15 mRNAs which, together, represent 10–20% of the total mRNA mass); (2) intermediate (consisting of approximately 1–2, 000 mRNAs which, together, represent 40–45% of the total mRNA mass), and (3) complex (consisting of approximately 15–20,000 mRNAs which, together, represent 40–45% of the total mRNA mass). Davidson and Britten, SCIENCE 204: 1052–1059 (1979). Differential levels of mRNAs within a cell is a significant obstacle to the identification and sequencing of low-abundance mRNA species. In the creation of nucleic acid libraries suitable for sequencing, superprevalent mRNAs impede the isolation and analysis of lower abundance mRNAs. Since the majority of clones isolated from a cDNA library will be from superprevalent and intermediate prevalent mRNAs, significant time and effort is spent resequencing previously known prevalent mRNA species, and large numbers of mRNA species must be sequenced in order to isolate and sequence low-abundance mRNA species. Thus, the rate of gene discovery from libraries is limited by the redundant nature of mRNAs present in a given cell. The presence of highly abundant mRNAs also hinders the comparison of differences in active genes observed in different cells of related tissue types, cells in varying stages of development, the effect of stimuli, and differential gene expression between normally functioning and abnormal cells (e.g., cells from normal tissue compared to tumor tissues).

One method for reducing the variation in the abundance of the individual nucleic acid molecules in a library is to produce a normalized library. Two approaches for generation of normalized libraries have been proposed. Weissman, MOL. BIOL. MED. 4: 133–143 (1987). These techniques include (1) hybridization to genomic DNA, in which the frequency of each hybridized cDNA in the normalized library is proportional to that of each corresponding gene in the genomic DNA, and (2) a kinetic approach that relies on the difference in annealing kinetics between abundant and rare species (Galau et al., ARCH. BIOCHEM. BIOPHYS. 179: 584–599 (1977). Several investigators employ the kinetic approach. For example, Soares et al. use single-stranded circles in their approach (see, e.g., U.S. Pat. Nos. 5,846,721 and 5,830,662), while Li et al. use haptenylated nucleic acid molecules (PCT application WO 99/15702). An alternative approach uses reassociation of short double-stranded cDNAs. Ko, NUCLEIC ACIDS RES. 18: 5705–5711 (1990).

Although normalization increases the chance of sequencing low-abundance nucleic acids, at best, the relative concentration of all mRNA species of a normalized library are within one to two orders of magnitude. Accordingly, the super- and intermediate-abundance nucleic acids are well represented in the library. Any attempt to randomly select and sequence clones from a normalized library will result in the selection of a high percentage of previously-characterized high abundance nucleic acid species.

Therefore, a need remains in the art for a method of rapidly and efficiently identifying and discarding previously-identified clones, thereby eliminating the redundancy in a population of nucleic acid molecules. Such a method would avoid the need to continuously re-sequence previously-characterized nucleic acid fragments and would permit the rapid and efficient identification and sequencing of novel genes.

SUMMARY OF THE INVENTION

The present invention relates to a highly efficient, high-throughput method for the identification and elimination of redundancy in a population of nucleic acid molecules using microarrays. The method comprises providing a random sample of nucleic acid fragments, immobilizing the random sample of nucleic acid fragments on a microarray, hybridizing one or more labeled probes corresponding to previously arrayed or sequenced fragments, detecting fragments hybridized to the labeled probes and identifying at least one fragment not hybridized or weakly hybridized to the labeled probes; and sequencing an identified fragment that was not hybridized or was weakly hybridized to the labeled probes. The nucleic acid fragments may be RNA or DNA, and may be cloned into a vector or not. In some embodiments, the nucleic acid fragments are members of a cDNA or genomic library, which may be normalized or non-normalized. In other embodiments, the nucleic acid fragments are PCR fragments. In many embodiments, the nucleic acid fragments are amplified, e.g., by PCR.

The nucleic acid fragments are then immobilized to a solid surface, in a microarray. The solid surface is preferably glass. Labeled probes that correspond to previously arrayed or sequenced fragments (i.e., the subtraction probe) are hybridized to the immobilized nucleic acid fragments. Nucleic acid labels may be fluorescent, luminescent, or radioactive labels, biotinylated, haptenated, or other chemical tags which allow for easy detection of labeled probes. Generally, the unhybridized probes are removed. Nucleic acid fragments that are not hybridized or are weakly hybridized to a labeled probe are isolated and are then pooled with the previous set of probes to generate a new, larger probe set. Usually, the newly isolated fragments are sequenced and their sequences compared to those found in a sequence database.

The methods of the present invention involve a subtraction protocol that identifies and isolates non-redundant nucleic acid fragments from a population of nucleic acid molecules. In most embodiments, the protocol is reiterated, in order to create a set of fragments that becomes more biased toward previously uncharacterized genes with each successive round. Accordingly, with each round of subtraction, probes corresponding to the newly isolated fragments are labeled and added to the previous subtraction probe, and this new subtraction probe is hybridized to the next microarray containing randomly picked nucleic acid fragments. This procedure is repeated several times, always adding the newly identified sequences to the previous subtraction probe. Thus, the method allows the identification and isolation of non-redundant or minimally overlapping nucleic acid fragments from sources of interest and enhances the rate of novel gene discovery. In a preferred embodiment, the non-redundant clones that are isolated using the methods of the invention are identified, selected, and immobilized to a new microarray to produce a unigene gene set.

Numerous applications can be envisioned for this invention. Specifically, any application in which the practitioner desires to enrich for sequences of interest or remove undesired nucleic acid fragments is amenable to the methods of the invention. A non-limiting set of uses includes:

I. A microarray-based method for enhancing the rate of discovery of expressed mRNA/cDNA sequences and facilitating construction a "Unique Gene" set. This method allows for increase novel gene discovery of expressed cDNAs and expedited construction of a Unique Gene set of expressed cDNAs.

II. A microarray-based method for enhancing the rate of discovery of genomic sequences and facilitating isolation of a DNA fragments corresponding to a whole genome or subregions of interest. In this application, the method provides for increased discovery of genomic clones, expedited construction of a set of non redundant or minimally tiled genomic clones, increased discovery of clones mapping to a region of interest, expedited construction of a set of genomic clones in a region of interest in the genome, and expedited filling of gaps in genomic maps (to facilitate disease gene mapping and disease gene identification).

III. A microarray-based method for enrichment and/or isolation of DNA sequences (mRNA/cDNA, genomic, extrachromosomal, plasmid and all other) that are unique to a population compared to another population. The invention also allows for identification of sequences (expressed cDNA or genomic) unique or novel to one organism versus another, including nucleic acid molecules from different strains (i.e. pathogenic vs. non-pathogenic) and different species.

IV. A microarray-based method for increasing discovery of related (or conserved) DNA sequences (mRNA/cDNA, genomic, extrachromosomal, plasmid and all other). Conversely, the method allows for identification of related sequences among closely or distantly related organisms.

V. A microarray-based method for enhancing the rate of removal of undesired sequences. In another embodiment, the invention provides for removal of undesired DNA sequences, including contaminating DNA sequences and sequences closely related to those previously identified.

VI. A microarray-based method for identifying changes in copy number (under or over represented) of DNA sequences (genomic, extrachromosomal, plasmid and all other) between different sources of nucleic acids.

DETAILED DESCRIPTION OF THE INVENTION

For convenience, the intended meaning of certain terms and phrases used herein are provided below.

"Known genes" or "known sequences" are those whose sequences can be found in a public or private sequence database.

"Novel genes" or "novel sequences" are those which are not found in any public or private sequence database.

"Weakly" hybridizing, as defined herein, refers to a hybridization signal that has a signal-to-noise (S/N) ratio of less than 0.5, as identified using the data analysis system of ArrayVision software. S/N is a measure of the background subtracted intensity of the spot signal divided by the standard deviation of the background intensity. A value of S/N less than 0.5 typically indicates no significant hybridization of a probe molecule to the particular DNA sample.

"Unique gene set" is a set of genes wherein each member of the set is represented once. A unique gene set from a particular cell type contains one copy of each gene expressed in that cell type.

"Complex probe" is one that contains many different DNA or RNA molecules. As used herein, the complex probe contains nucleic acid sequences that are complementary to known sequences.

The present invention provides a highly efficient, high-throughput method for the identification and elimination of redundancy in a population of nucleic acid molecules using reiterative selection involving subtractive hybridization with a complex probe pool and microarray technology. Randomly-chosen nucleic acid fragments chosen from a cloning library are microarrayed and exposed, under hybridizing conditions, to a complex labeled probe generated from known sequences (e.g. sequences obtained from a public database such as Genbank, pubEST). Only clones that do not hybridize to this first probe pool are sequenced; clones that hybridize to this first probe pool are not sequenced. The sequences obtained in this step are compared to public databases of previously-identified nucleic acid molecules (e.g. BLAST, pubEST, Genbank NR, Incyte). These sequences are added to the initial probe pool to generate a second, subtractive probe pool. This subtractive probe pool is hybridized to a second group of randomly-chosen clones from the library. The probe hybridizes to the nucleic acids complimentary to the nucleic acids of the initial, publicly known sequences, as well as to the nucleic acids identified in the first round of hybridization. The procedure of expanding the probe pool after successive rounds of hybridization is repeated until essentially all randomly-chosen clones hybridize to a labeled probe, indicating that all of the previously uncharacterized clones have been sequenced. Accordingly, the methods of the present invention eliminate the need to re-sequence known clones—a problem that reduces the efficiency of other methods known in the art.

The first step involves isolation of randomly-chosen nucleic acid fragments from a population of nucleic acid molecules. These fragments may be DNA or RNA, and they may be cloned into vectors or not. In a preferred embodiment, the nucleic acid molecules comprise cDNA from a nucleic acid library of unknown sequences. In one embodiment, the library is a genomic library. In another embodiment, the library is a cDNA library. In either embodiment, the library can be a normalized library, or a non-normalized library. Alternatively, the population of nucleic acid fragments may not be part of a library, e.g., PCR fragments.

In some embodiments, the nucleic acids are amplified, using PCR or other amplification methods. The DNA is then immobilized in a microarray on a surface, preferably glass. In some embodiments, the arrayed DNA comprises oligonucleotides synthesized on glass. In a preferred embodiment, the PCR fragments are arrayed using a microarray spotter.

These surface-immobilized DNA molecules are then allowed to contact a labeled probe pool containing nucleic acid molecules of known or defined sequences under conditions which permit hybridization. Standard labeling protocols for nucleic acids are described, e.g., in Sambrook et al.; Kambara et al., BIOTECHNOLOGY 6: 816–821 (1988); Smith et al., Nuc. ACIDS RES. 13: 2399–2412 (1985). Nucleic acid labels may be fluorescent, luminescent, or radioactive labels, biotinylated, haptenated, or other chemical tags which allow for easy detection of labeled probes. Fluorescent labels are advantageous for the methods described herein, as these are routinely used with automated instrumentation for simultaneous high throughput analysis of multiple samples. Metzker and Gibbs have recently disclosed a family of fluorescently tagged nucleotides based on the Cy fluorophores with improved spectral characteristics. U.S. Pat. No. 5,728,529, incorporated herein by reference. Alternative sets of fluorophores include: the rhodamine based fluorophores, TARAM, ROX, JOE, and FAM; the BigDye® fluorophores (Applied Biosystems, Inc.), the dansyl group, fluorescein and substituted fluorescein derivatives, acridine derivatives, coumarin derivatives, pthalocyanines, tetramethylrhodamine, Texas Red®, 9-(carboxyethyl)-3-hydroxy-6-oxo-6H-xanthenes, DABCYL® and BODIPY® fluorophores (Molecular Probes, Eugene, Oreg.).

Subsequent to the hybridization step, the amount of label is detected at each position in the microarray. A key feature of the technology described here is the use of DNA microarrays. See Brown and Botstein, NAT. GENET. 21: 33–37 (1999). Microarrays are an ordered array of double stranded or single stranded DNA molecules positioned on a support material in a spatially separated organization. In contrast to filter "macroarrays", which are typically large sheets of nitrocellulose, microarrays position the DNA more densely packed organization such that up to 10000 DNA molecules can be fit into a region typically 1–4 square centimeters. Microarrays typically use coated glass as the solid support, in contrast to the nitrocellulose-based material of filter arrays. By having an ordered array of DNA samples, the position of each sample can be tracked and linked to the original sample from which the DNA on the array was generated. Methods and apparatus for preparing a microarray have been described. See, e.g., U.S. Pat. Nos. 5,445,934 and 5,800,992, both incorporated herein by reference.

The process of creating a microarray involves a series of steps in which a set of bacterial colonies containing a cDNA library are processed to obtain an amplified fragment of purified DNA derived from the insert of the vector held in any one bacterial colony. The series of steps can be carried out either manually or through the use of robotic workstations, such as PCR machines, and liquid handling robots. In the preferred method, the steps are carried out using multiwell plates made up of 96 wells, 384 wells, or 1536 wells. However, other configurations are possible. The microarray is constructed using a robotic spotter such as the instrument developed by Molecular Dynamics or in the laboratory of Patrick Brown, Stanford University (ibid). Another key feature of the microarray process is that the data analysis is performed automatically using data analysis software, such as ArrayVision. The entire process from clone tracking, microarray construction, to results is fully integrated so that bacterial colonies to be processed for sequencing can be readily identified.

The current technology for microarray construction positions up to 10,000 DNA samples per microarray. With future improvements to the technology, it will be possible to position many more samples than this, perhaps 100,000 per microarray. The DNA samples on the microarray are hybridized with RNA or DNA probes that have been fluorescently labeled to identify whether the probe sample contains a molecule that is similar or identical to the DNA sample on the microarray. A key feature of the system is that a complex probe can be hybridized to the microarray. A complex probe is one that contains many different DNA or RNA molecules. Under the appropriate conditions, probe molecules hybridize to a DNA molecule on the microarray. Generally, identical or near identical sequences form productive hybrids. The presence of DNA-probe hybrid molecules is detected by a fluorescence detection instrument. If the hybridization signal is weak or non-existent at a particular DNA site, then the corresponding DNA or RNA molecule in the probe is absent. Current microarray instruments can hybridize up to four different fluorescent probe samples at one time. With improvements to the technology, more probes can be hybridized at once.

There are several important features of the microarray-based subtraction method. For example, the process is accomplished by iterative rounds of microarray construction, hybridization, and analysis. The method reduces amount of sequencing to obtain a Unique gene set of a given size. It does this by removing duplicate cDNAs, samples with bacterial or mitochondrial DNA, and samples without any cDNA insert.

Up until recently, DNA hybridizations were performed on nitrocellulose filters. In contrast to microarrays where DNA is spotted directly onto the microarray, filter arrays are generated by spotting bacterial colonies on the filters, placing the filters over a agar growth media, and incubating the filters under conditions that promote the bacterial colonies to grow. The DNA within the bacterial colonies is released by lysing the colony and treating the filters to fix the DNA to the filter material. The process of generating a bacterial filter array can take typically 2–4 days.

There are a number of advantages of microarray-based subtraction versus filter array methods. For example, filter methods generally array bacterial colonies in which the cloned cDNA is contained. The colonies must be grown up over several days, lysed to release DNA and fix DNA onto the filter. Hybridization to filter arrays of colonies is less reliable due to bacterial debris and the low amount of DNA released from the colony. A second advantage is that the iterations are quicker with microarrays than with filters. This is due to the time needed to grow colonies on the filters and prepare them for the next round of hybridization. In contrast, probing of a subsequent microarray can begin less than 24 hr after analysis of an array is completed. Another advantage of microarrays is the ability to use fluorescently labeled probes. This provides for a non-radioactive method for hybridization detection. In contrast, filter hybridization generally uses probes labeled with radioactive phosphorus or sulfur. Microarrays can be hybridized with multiple probes simultaneously. In contrast, filter arrays can only be hybridized with one probe at a time. One of the most important advantages of microarrays is their reproducibility and sensitivity of hybridization signals. Typically, hybridization signals are higher and sensitivity is greater on microarrays versus filter arrays. This allows for the complexity of the probe to be higher and still get a positive hybridization signal on the microarray. This is a key feature for the microarray-based subtraction method. In addition, filter arrays often exhibit spurious background signals that are unrelated to productive hybridization between the probe and DNA on the filter.

There are a number of advantages of unique gene construction by microarray-based subtraction versus other methods. For example, methods using selective hybridization in solution, as used in cDNA normalization or subtraction procedures, typically result in the loss of certain low abundant clones. In contrast, using the iterative microarray-based subtraction approach, all clones in the library are capable of being identified. A low abundant cDNA clone will be found after multiple iterative rounds of hybridization. Another advantage of the microarray-based approach for preparation of unique gene sets of cDNAs is that the resulting cDNA clones are more likely to be near full length. In contrast, other methods for subtraction and normalization often enrich short, incomplete cDNAs.

A weak signal or no signal at all at a particular position of the array generally corresponds to the presence of DNA that has not hybridized or has weakly hybridized to sequences represented in the probe pool. Clones with a weak signal or no signal at all are sequenced. DNA sequencing methods are well known in the art. See, e.g., Maxam and Gilbert, PROC NATL ACAD SCI USA 74: 560–564 (1977); Sanger et al., PROC NATL ACAD SCI USA 74: 5463–5467 (1977); U.S. Pat. No. 5,821,058, incorporated herein by reference. Automated analysis of fragments in gels or capillaries has significantly reduced the labor involved in collecting and processing sequence information. See, e.g., Prober et al., SCIENCE 238: 336–341 (1987); Smith et al., NATURE 321: 674–679 (1986); Luckey et al., NUCLEIC ACIDS RES 18: 4417–4421(1990); Dovichi, ELECTROPHORESIS 18: 2393–2399 (1997). The nucleic acid fragments isolated and sequenced in this step are added into the initial probe pool. Often, these fragments are sequenced first to determine the presence of non-redundant nucleic acid molecules in the microarray. Their sequences are then compared to public databases of previously-identified nucleic acid molecules (e.g., BLAST, pubEST, Genbank NR, Incyte). This second subtractive probe pool is used in the next round of hybridization involving a second microarray generated from a different group of randomly-chosen clones from the library. By adding the newly identified nucleic acid fragments to the subtractive probe pool, subsequent microarrays of randomly-chosen clones from the library are exposed to a larger number labeled probes. Accordingly, methods of the present invention eliminate the re-sequencing of known clones—a problem that reduces the efficiency of other art-known methods. As the number of labeled probed increases with successive iterations, the number of labeled "known" clones will increase and fewer clones will be unlabeled. Eventually, with sufficient iterations, all of the clones in microarrays of randomly-chosen clones from a given library will be labeled, as all of the clones will have been sequenced.

Figure 1:
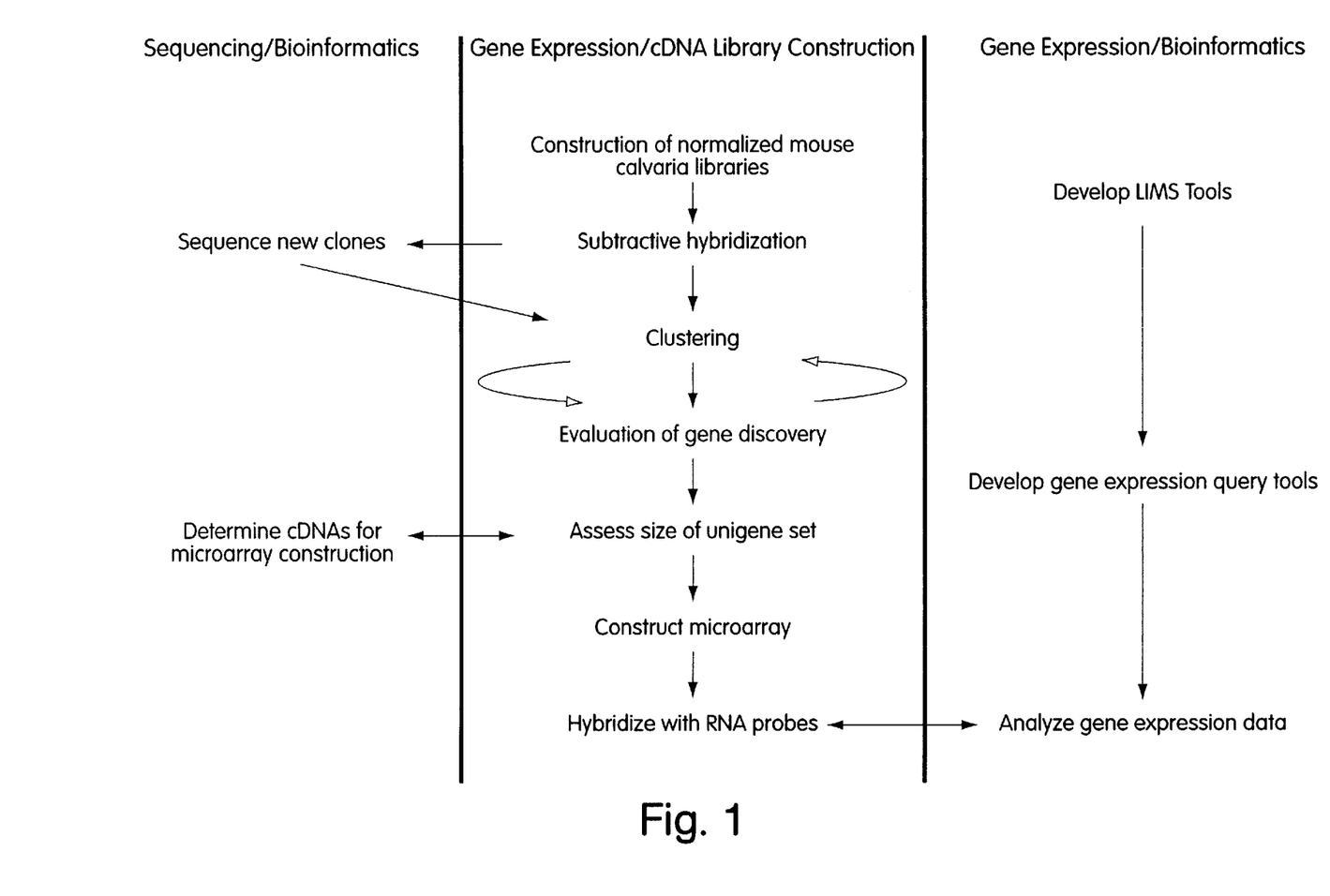
FIG. 1 is a flow chart depicting an overview of the gene discovery strategy.

In one aspect of the present invention, a cloning library enriched in low abundance mRNAs is generated. In an extension of this method, the low-abundance sequences are used in the construction of a unique gene chip for use in subsequent experimentation (e.g., differential display experiments). An overview of the strategy for the discovery of novel genes is depicted in FIG. 1. In an additional embodiment of the present invention, contaminating nucleic acids are removed from a cloning library.

The invention may be adapted to any purpose in which the practitioner desires to enrich for sequences of interest or remove sequences that are not of interest. Exemplary uses include, but are not limited to, the following:

I. A Microarray-based Method for Enhancing the Rate of Discovery of Expressed mRNA/cDNA Sequences and Facilitating Construction of a "Unique Gene" Set In one aspect, the invention provides for increased novel gene discovery and expedited construction of a Unique Gene set from expressed cDNAs. This can be accomplished by:

(a) amplifying (by PCR or nucleic acid isolation procedures) and providing a random sample of nucleic acid fragments;

(b) immobilizing the random nucleic acids on a solid surface in a microarray format;

(c) hybridizing labeled probes from a DNA source to the immobilized, microarrayed DNA fragments;

(d) detecting DNA fragments hybridized to a labeled probe and identifying at least one fragment that does not hybridize or hybridizes weakly (i.e., subtraction);

(e) determining the identity of the DNA fragment by DNA sequencing, hybridization or other analytic approaches; and (f) reiterating steps (b) or (c) through (e) with previously identified sequences in the probe set in order to identify additional sequences and increase the Unique Gene set.

II. A Microarray-based Method for Enhancing the Rate of Discovery of Genomic Sequences and Facilitating Isolation of a DNA Fragments Corresponding to a Whole Genome or Subregions of Interest In the case of genomic sequences, it may be desired to construct a set of "minimally tiled" clones, i.e., clones with the smallest amount of overlapping sequence possible. Thus, the invention allows for increased discovery of genomic clones, expedited construction of a set of non redundant or minimally tiled genomic clones and increased discovery of clones mapping to a gene of interest. The method also allows expedited construction of set of genomic clones in a region of interest in the genome. The ability to easily map clones to a region of interest in the genome further enables the practitioner to easily fill gaps in a genomic map, facilitating disease gene mapping and disease gene identification.

The method comprises:

(a) amplifying (by PCR or nucleic acid isolation procedures) and providing a random sample of genomic nucleic acid fragments;

(b) immobilizing the random nucleic acids on a solid surface in a microarray format;

(c) hybridizing labeled probes (pooled or single) from a DNA source to the immobilized, microarrayed DNA fragments (probes can be cDNA/mRNA or genomic sequences);

(d) detecting DNA fragments which hybridize to a labeled probe;

(e) determining the identity of the DNA fragment by DNA sequencing, hybridization or other analytic approaches; and (f) reiterating steps (b) or (c) through (e) with previously identified sequences in the probe set in order to identify additional sequences and increase the Unique Gene set.

In particular, end regions of previously identified sequences can be used as probes to "walk" and identify flanking clones.

III. A Microarray-based Method for Enrichment and/or Isolation of DNA Sequences (mRNA/cDNA, Genomic, Extrachromosomal, Plasmid and All Other) That are Unique to a Population Compared to Another Population.

Another use of the invention is for the identification of sequences (expressed cDNA or genomic) unique or novel to one organism versus another. This includes identification of nucleic acids unique to one strain vs. another (i.e., pathogenic vs. non-pathogenic), as well as comparison of unique gene sets from closely related species and more distantly related species.

Since nucleic acid molecules from more than one source organism are used in this application, the specific steps of the method are somewhat different and include:

(a) amplifying (by PCR or nucleic acid isolation procedures) and providing a random sample of nucleic acid fragments;

(b) immobilizing the random nucleic acids on a solid surface in a microarray format;

(c) hybridizing labeled probes from source #1 and from source #2 to the immobilized, microarrayed DNA fragments (probes can be cDNA/mRNA or genomic sequences);

(d) detecting DNA fragments which hybridize to a labeled probe from source #1 but not Source #2 or visa versa; and (e) determining the identity of the DNA fragment by DNA sequencing, hybridization or other analytic approaches.

IV. A Microarray-based Method for Increasing Discovery of Related (or Conserved) DNA Sequences (mRNA/cDNA, Genomic, Extrachromosomal, Plasmid and All Other)

The converse to the above method allows discovery of related sequences (rather than differences) in various species, including different bacterial strains and distantly related organisms. Again, the method comprises:

(a) amplifying (by PCR or nucleic acid isolation procedures) and providing a random sample of nucleic acid fragments;

(b) immobilizing the random nucleic acids on a solid surface in a microarray format;

(c) hybridizing labeled probes (single or pooled) to the immobilized, microarrayed DNA fragments, particularly at decreased hybridization stringencies (probes can be cDNA/mRNA or genomic sequences);

(d) detecting DNA fragments which hybridize to a labeled probe (often with a weaker signal);

(e) determining the identity of the DNA fragment by DNA sequencing, hybridization or other analytic approaches; and (f) comparing DNA sequences obtained to other available DNA sequences to detect sequences which show homology but are not identical to other known sequences.

V. A Microarray-based Method for Enhancing the Rate of Removal of Undesired Sequences The invention also provides for removal of undesired DNA sequences (cDNA or genomic) from any population of arrayed DNA. This may include contaminating DNA, as well as any DNA not of interest, e.g., sequences closely related to those already identified. This method comprises:

(a) amplifying (by PCR or nucleic acid isolation procedures) and providing a random sample of nucleic acid fragments;

(b) immobilizing the random nucleic acids on a solid surface in a microarray format;

(c) hybridizing labeled probes, which are sequences targeted for removal, to the immobilized, microarrayed DNA fragments;

(d) detecting DNA fragments hybridized to a labeled probe and identifying at least one fragment that does not hybridize or hybridizes weakly (i.e., subtraction);

(e) determining the identity of the DNA fragment by DNA sequencing, hybridization or other analytic approaches; and (f) reiterating steps (a), (b) or (c) through (e) with previously identified sequences in the probe set, as deemed necessary, in order to eliminate unwanted sequences from the population of fragments.

VI. A Microarray-based Method for Identifying Changes in Copy Number (Under or Over Represented) of DNA Sequences (Genomic, Extrachromosomal, Plasmid and All Other) Between Different Sources of Nucleic Acids.

The present invention also provides a microarray-based method for identifying changes in copy number (under or over represented) of DNA sequences (genomic, extrachromosomal, plasmid and all other) between different sources of nucleic acids. The method comprises:

(a) amplifying (by PCR or nucleic acid isolation procedures) and providing a random sample of nucleic acid fragments from a given source;

(b) immobilizing the random nucleic acids on a solid surface in a microarray format;

(c) hybridizing labeled probes (single or pooled; any type of nucleic acid—mRNA/cDNA, genomic, extrachromosomal, plasmid and all other—generally corresponding to the type of nucleic acid arrayed) from another source to the immobilized, microarrayed DNA fragments;

(d) detecting DNA fragments which show absent, significantly lesser or significantly greater hybridization to a labeled probe. Such alterations in signal intensity will reflect changes in abundance; and (e) determining the identity of the DNA fragment(s) by DNA sequencing, hybridization or other analytic approaches.

EXAMPLE 1 cDNA Microarray Construction 1.1 cDNA Amplification

A cDNA library was generated by techniques well known in the art. cDNA inserts were isolated from bacterial clones using Polymerase Chain Reaction (PCR). Twenty five $\mu$l of PCR mix was added to each well of a 384 well microtiter plate from a PCR master mix containing 1000 µl 10× PCR Buffer, 800 µl of 2.5 mM dNTPs, 400 µl T3 primer (5 pmoles/µl), 400 µl of T7 primer (5 pmoles/µl), and 10 µl recombinant Taq polymerase. The PCR plate was inoculated from the overnight growth plate using a 384 pin tool to transfer approximately 1 µl. Plates were sealed with MicrosealA and placed in alpha units of MJ Research tetrad PCR machines. Reactions were preheated at 95° C. for 4 min, followed by 35 cycles of amplification: 45 sec at 95° C., 1 min at 55° C., and 2.5 min at 72° C.

Amplification of the cDNA inserts was verified by agarose gel electrophoresis in which 2 µl of each PCR reaction was loaded onto a 1% agarose gel containing 500 ng/µl ethidium bromide. 500 ng of molecular weight standard (1 Kb ladder, Promega) was added to each gel for size determination and quantitation of amplification. Samples were electrophoresed in 1× TAE (Tris Acetate, EDTA) at 150 milliamps for 30 min.

Amplified cDNA inserts were purified from unincorporated nucleotides and primers in 384 well glass fiber filter plates as follows: 70 µl of 5 M guanidinium isothiocyanate (Sigma) was added to each plate using a 96 pin Cyclone liquid handler; 25 µl of PCR reaction was transferred from the PCR microtiter plate to the glass fiber filter plate and incubated for 2 min at room temperature. The filter plate was placed on a vacuum manifold and dried. The filter plate was washed 2 times with 70 µl of 80% isopropanol and dried on a vacuum manifold for two min. The purified PCR product was eluted from the glass fiber plate into a 384-well collection plate by addition of 50 µl of water, incubation for 5 min at room temperature, and centrifugation at 3000 rpm for 5 min. Purified PCR products were lyophilized down to dryness in a speed-vac on high for 45 min to 1 hour. Purified products were resuspended in 30 µl of 50% DMSO/water.

1.2 Immobilization of the Sample

A maximum of 4,608 different PCR fragments were spotted onto glass slides in duplicate using a Generation III (Gen III) microarray spotter from Amersham/Molecular Dynamics. Twelve 384-well U bottom microtiter plates were placed in the hotel of the Gen III spotter. Up to 36 glass slides were placed on the spotter and spotted with DNA while the spotting humidity of the spotting chamber was maintained at 55%. Six slides were spotted per source plate access. Prior to accessing the next set of PCR templates, the 12 pen cassette was washed as follows: 1 sec in 0.2 M KOH, 1 sec in 95% ethanol, and 2 sec in distilled water. After spotting, slides were air dried for 1 hour at room temperature. The PCR fragments were cross linked to the glass by UV crosslinking in a Stratalinker (Stratagene) at 5000 joules.

EXAMPLE 2

Probe Synthesis

The cDNA inserts for sequence verified clones were amplified in 96-well PCR plates as previously described for 384-well plates, with the exception that the PCR reaction volume was 50 µl. Amplification was verified by agarose gel electrophoresis as previously described. PCR fragments were purified using 96-well carbon fiber filter plates and a DNA binding resin as follows: 100 µl of Wizard PCR purification resin (Promega) was added to each well of a 96-well filter plate using a 12 channel pipettor; the 50 µl PCR reaction was added to the resin, and incubated at room temperature for 1 min; the plate was then placed on a vacuum manifold for 1 min, until dry. Each plate was briefly washed with 200 µl of 80% isopropanol before the solution was removed by vacuum manifold, and the filter plate was well dried by vacuum. Purified PCR product was eluted by addition of 50 µl of sterile, distilled water followed by centrifugation at 3000 rpm for 5 min into a 96-well microtiter plate. The purified PCR reactions were pooled and 100 µg of the pooled PCR reaction was purified over Qiagen PCR purification columns. The repurified PCR pool was verified by gel electrophoresis as previously described. The concentration of the pooled PCR was determined spectrophotometrically and the concentration adjusted to 100 ng/µl using sterile, distilled water.

The purified PCR fragment pool was used as a template for RNA synthesis in an in vitro transcription reaction. Purified PCR reaction (500 ng) was added to a 20 µl reaction containing 1× transcription buffer, 0.5 mM of each rNTP, 37 mM DTT, and 10 units of T7 or T3 RNA polymerase. The reaction was incubated at 37° C. for 90 min. The DNA template was removed by addition of 1 unit of RQ1 DNase and incubation at 37° C. for 30 min. The unincorporated nucleotides were removed by purification over an RNA Easy Column (Qiagen).

A fluorescent probe was synthesized from the in vitro synthesized RNA template in a first strand labeling reaction as follows: 100 ng of RNA template was incubated with 0.5 µg random hexamers in a final volume of 10 µl for 10 min at 70° C. The reaction was chilled on ice for 5 min, followed by the addition a reaction mix containing 1× Reverse transcription buffer (20 mM Tris pH 8.4, 50 mM KCl, 2.5 mM $MgCl_2$), 10 mM DTT, 100 µM dGTP, dTTP, dATP, 50 µM dCTP, 50 µM Cye3 dCTP or cye5 dCTP, and 200 units of Superscript II reverse transcriptase (Gibco BRL, #18089-011). The reaction was incubated at 42° C. for 90 min. The RNA template was hydrolyzed by the addition of 1 µl of 5 M NaOH and incubation at 37° C. for 10 min. The NaOH was neutralized by adding 10 µl of 2 M MOPS (free acid). Unincorporated nucleotides and primers were removed by purification over GFX columns (Pharmacia). Probes were lyophilized down and resuspended in 30 µl of hybridization buffer containing 50% formamide, 5× SSC, 0.2% SDS, 1× Denhardt's, 100 µg/ml salmon sperm DNA, and 1 µg oligo-dA(80).

EXAMPLE 3

Identification of Novel Genes

Figure 2:
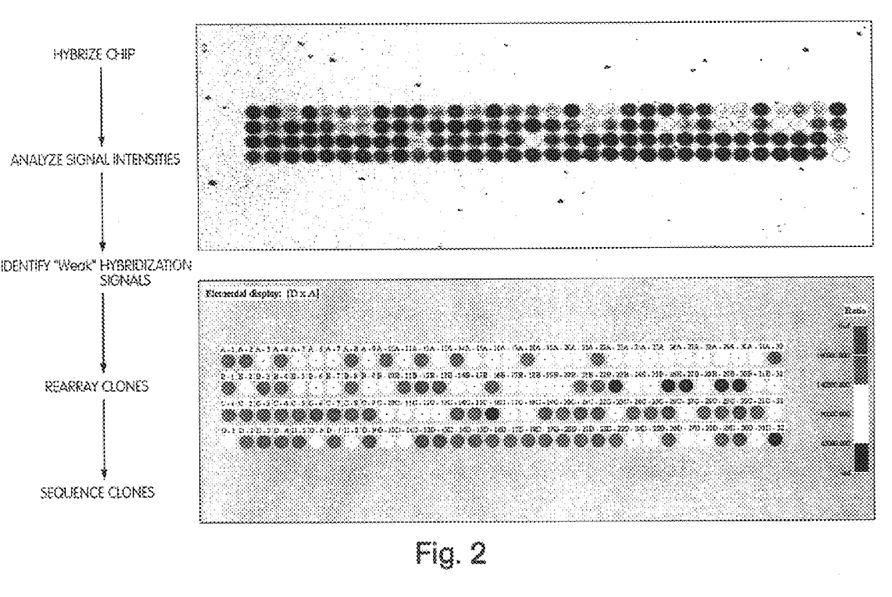
FIG. 2 is a representation of a microarray used in the identification of novel genes.

The procedure for identifying novel genes is depicted in FIG. 2.

3.1 Hybridization

Probes were denatured at 100° C. for 10 min and added to the microarray slide. Slides were covered with glass cover slips (Corning) and incubated for 18 to 24 hours at 42° C. in a humidified chamber. Hybridized slides were washed twice in 2× SSC containing 0.1% SDS for 10 min at room temperature, followed by 2 washes in 0.1× SSC containing 0.1% SDS at 42° C. for 10 min. Slides were dipped several times in distilled water and dried under filtered high pressure air. Hybridization of fluorescent probes was detected by scanning the slides in a Generation III (Gen III) confocal scanner (Amersham/Molecular Dynamics).

3.2 Data Acquisition

Slide images were analyzed with ArrayVision image analysis software (Imaging Research) for spot finding analysis, localized background determination, distribution of signal intensities in a spot, and signal to noise ratios. Data was exported as a tab-delimited file and exported to an Oracle database. Normalization and statistical quality assessment was performed with a Web-based set of data analysis tools and data was analyzed with Web browser tools developed in the Hoechst-Ariad Genomics Center. Data was sorted based on signal to noise ratio, and DNAs which had a signal above background but below a threshold signal to noise ratio were further characterized by EST sequencing.

3.3 Sequencing and Comparison to Known Libraries

Clones which did not hybridize in step 3.1 were targeted for EST (expressed sequence tag) sequencing, using techniques well-known in the art. Adams et al., SCIENCE 252: 1651–1656 (1991). Sequences were searched against the public dbEST, mouse EST, and Lifeseq (Incyte) databases. All clones which were newly characterized or identified as previously-known sequences were added to the probe (subtraction) pool to prevent multiple identification of the same gene during subsequent hybridizations.

3.4 Reiterative Subtractive Hybridization

The next microarray containing randomly picked clones was hybridized to a new probe which included all the previous clones, and in addition contained any new clones identified from EST sequencing. The clones identified from this methodology were used for building unique gene [Ermolaeva et al., NAT. GENET. 20: 19–23 (1998)] sets containing clones previously identified from other sources (e.g., public databases or Incyte) as well as novel clones which had not been previously described.

EXAMPLE 4

Selection of Low Abundance mRNAs

A reiterative-based subtraction protocol was used where microarrays were constructed which contained 1500 different cDNAs randomly picked from a cDNA library. The first microarray was hybridized with a subtraction probe containing cDNAs encoding 64 housekeeping and ribosomal genes. Non-hybridizing clones were analyzed by EST sequencing. Any clones which were not present in the previous subtraction probe were added to the existing subtraction probe and hybridized to the next microarray containing randomly picked cDNA clones. This procedure was repeated 17 times, so that a total of 26,112 cDNAs were microarrayed. Based on the hybridization data, only 7,700 clones were chosen for EST sequencing. After clustering, 4,400 different cDNA clones were identified. This group of clones was highly enriched for low abundance transcripts. Additionally, by removing the redundant high abundance messenger RNAs, the microarray-based subtraction decreased the EST sequencing effort by 70%.

EXAMPLE 5

Construction of a Unique gene Chip, use in Differential Display

Figure 3:
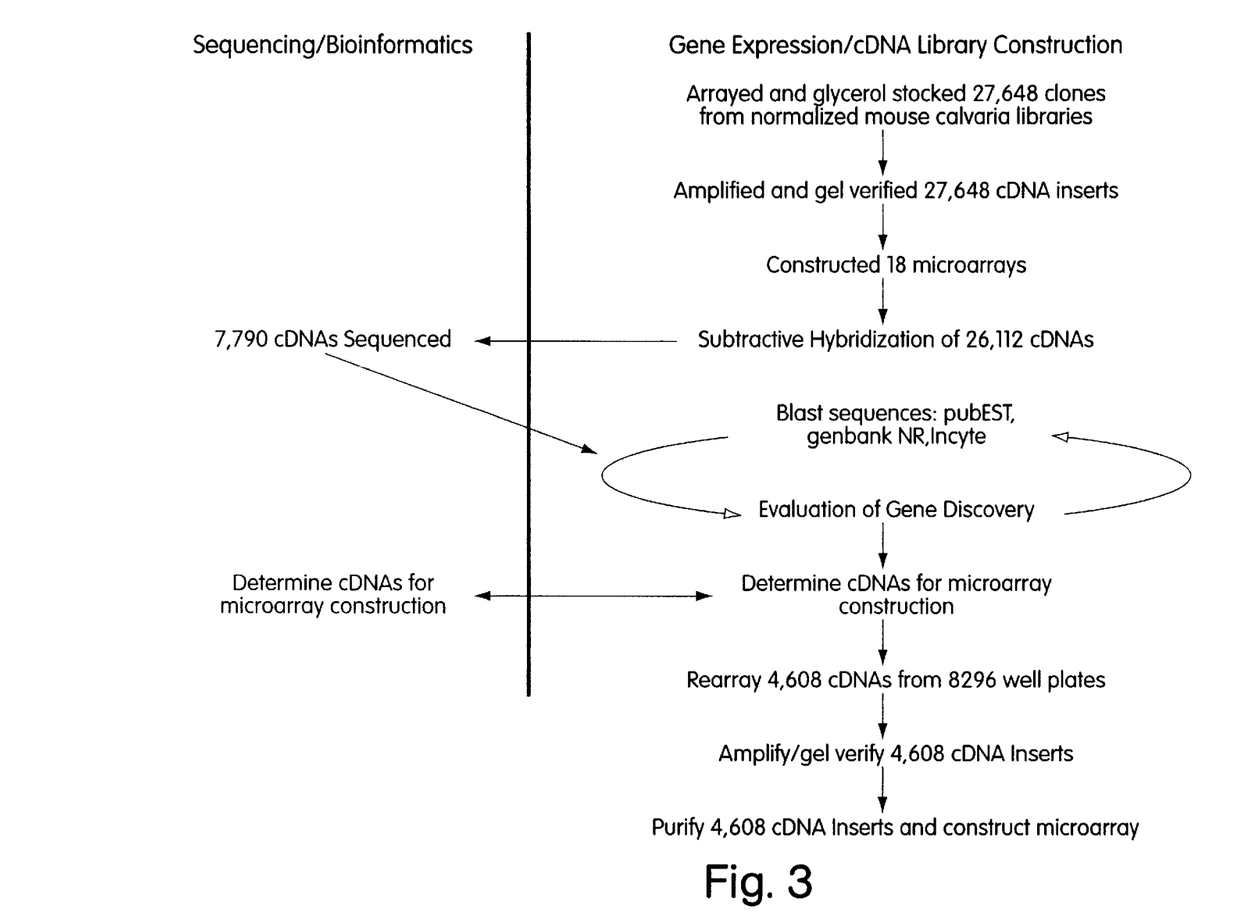
FIG. 3 is a flow chart depicting the construction of a mouse calvaria unique gene chip.

A mouse calvaria unique gene chip was constructed according to the procedure outlined in FIG. 3. Arrays were generated of 27,648 clones from normalized mouse calvaria libraries. All 27,648 clones were PCR amplified and arranged into 18 microarrays. As a result of subtractive hybridization (as outlined above), 7,790 cDNAs were sequenced following 18 rounds of hybridization. Upon comparison of these sequences to databases containing known sequences, 4,608 clones were chosen for amplification and placement on a microarray. This unique gene chip was then used in a differential gene expression experiment to identify genes modulated by BMP2 (bone morphogenic protein 2).

EXAMPLE 6

Removal of Library Contamination

Figure 4:
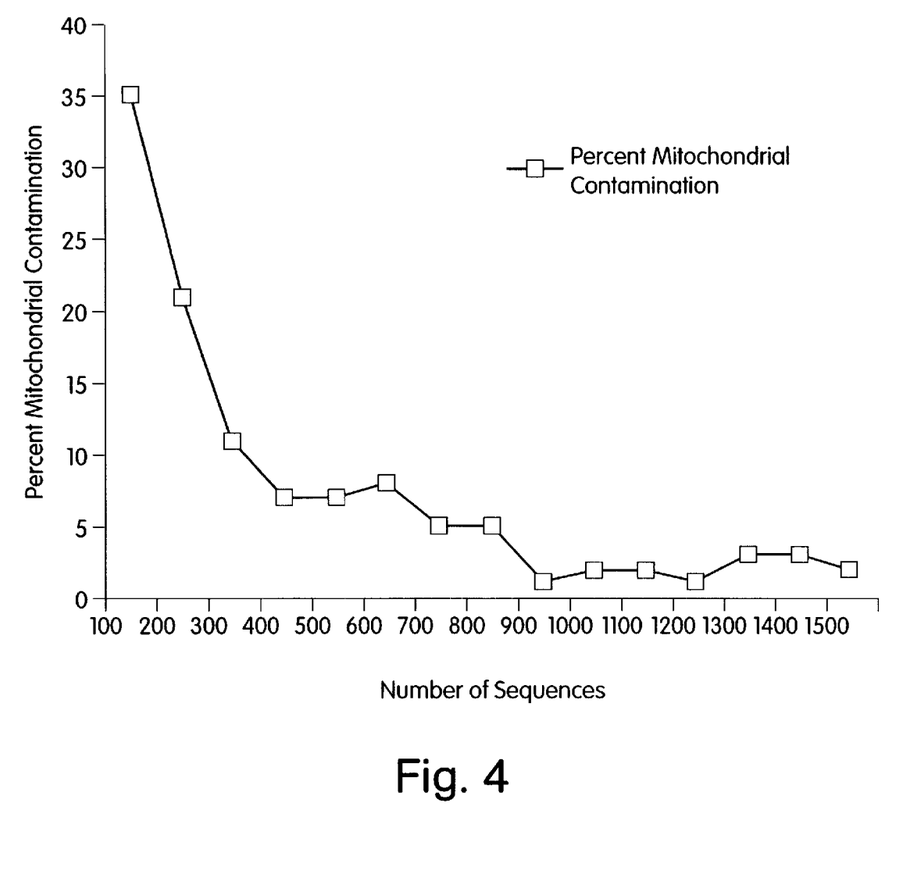
FIG. 4 is a line graph depicting the removal of contaminating mitochondrial genes from a library.

The subtractive hybridization protocol as described by the current invention was demonstrated in the removal of contamination of highly abundant genes from a cloning library. As shown in FIG. 4, the initial library was contaminated by 35% of mitochondrial genes. After nine rounds of subtractive hybridization, this amount was reduced to 2–3%, demonstrating the usefulness of the current invention in improving the quality of this cloning libraries.

Equivalents

From the foregoing detailed description of the specific embodiments of the invention, it should be apparent that a unique method of gene isolation has been described. Although particular embodiments have been disclosed herein in detail, this has been done by way of example for purposes of illustration only, and is not intended to be limiting with respect to the scope of the appended claims which follow. In particular, it is contemplated by the inventor that various substitutions, alterations, and modifications may be made to the invention without departing from the spirit and scope of the invention as defined by the claims. For instance, the choice of the particular source of nucleic acid, the particular label, or the particular probe pool is believed to be a matter of routine for a person of ordinary skill in the art with knowledge of the embodiments described herein.

What is claimed is:

1. A method of enhancing the rate of novel gene discovery in a population of previously-uncharacterized nucleic acid molecules, comprising a. contacting an first ordered array of nucleic acid samples from said population with an initial complex subtraction probe pool, said probe pool comprising a labeled probe corresponding to a redundant or known sequence;

b. identifying a nucleic acid, said nucleic acid being characterized by weak or no hybridization to said initial complex subtraction probe pool;

c. sequencing said nucleic acid to yield a newly-identified sequence;

d. adding said newly-identified sequence to said initial pool to generate a second complex subtraction probe pool, said second pool comprising a larger number of labeled probes compared to said initial pool;

e. contacting a second ordered a array of nucleic acid samples from said population with said second subtraction probe pool; and f. repeating steps b.-e., wherein each repeat of steps b.-e. reduces the redundancy of said population of previously-uncharacterized nucleic acid molecules, thereby enhancing the rate of novel gene discovery.

2. The method of claim 1, wherein said redundant or known sequence is selected from the group consisting of a public database member gene, a housekeeping gene or ribosomal gene.

3. The method of claim 1, wherein said first and said second ordered array comprise DNA immobilized on a glass surface.

4. The method of claim 1, comprising repeating steps b.-e. to generate a set of genes wherein each member of the set is represented once.

5. The method of claim 1, wherein said weak hybridization comprises a signal-to-noise ration of less than 0.5.

* * * * *